US00PP13285P2

(12) United States Plant Patent
Pittman

(10) Patent No.: US PP13,285 P2
(45) Date of Patent: Nov. 26, 2002

(54) *ABELIA×GRANDIFLORA* VARIETY NAMED 'GOLDENGLOSSY'

(75) Inventor: Jerry Brunson Pittman, Mobile, AL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 09/902,723

(22) Filed: Jul. 12, 2001

(51) Int. Cl.[7] ..... A01H 5/00
(52) U.S. Cl. ..... Plt./226
(58) Field of Search ..... Plt./226

*Primary Examiner*—Kent L. Bell

(57) ABSTRACT

A new and distinct variety of *Abelia×grandiflora* plant which possesses a compact growth habit, variegated foliage, fragrant white flowers, reddish-orange pigmentation of the new growth terminals and winter foliage, and attractive reddish-purple immature stems.

1 Drawing Sheet

BACKGROUND OF THE INVENTION

The present invention relates to a new and distinct cultivar of Abelia, botanically known as *Abelia×grandiflora,* and hereinafter referred to by the cultivar name 'Goldenglossy'. This new Abelia variety was discovered by Jerry Brunson Pittman in May, 1996 as a branch sport of *Abelia×grandiflora* 'Sherwoodii', an unpatented variety maintained by Plant Development Services Inc. in Loxley, Ala. The value of this new cultivar lies in its compact growth habit, unique variegated foliage, reddish-orange pigmentation of the new growth terminals and winter foliage, and reddish-purple pigmentation of the immature stems. 'Goldenglossy' has retained many of the outstanding attributes of the parent cultivar, in particular its tolerance of drought, insects, and diseases which makes it adaptable to culture in the Sunbelt states.

Asexual propagation of the new plant by cuttings has been under Mr. Pittman's direction at the same location. The new plant retains its distinctive characteristics and reproduces true to the type in successive generations. The plant cannot be reproduced true from seed.

SUMMARY OF THE INVENTION

The following are the most outstanding and distinguishing characteristics of this new cultivar when grown under normal horticultural practices in Loxley, Ala.

1. The variegation of the foliage is unique and beautiful.
2. Compact growth habit.
3. New growth terminals and winter foliage are a reddish-orange color.
4. Immature stems are reddish-purple.
5. Easily propagated with semi-hardwood cuttings in late spring through the summer.
6. Medium to fast growth rate under normal fertilization and moisture conditions.
7. Performs well in sun or shade.
8. Ideal for mass plantings and low hedges.
9. Attractive fragrant white flowers.
10. Drought tolerant.
11. Relatively pest resistant.
12. Hardy to Zone 6.
13. Attracts butterflies.

DESCRIPTION OF THE DRAWINGS

This new *Abelia×grandiflora* variety is illustrated by the accompanying photographic prints in which:

1. The photograph at the top of the sheet is a close-up view of the unusual reddish-orange pigmentation of the immature leaves and the reddish-purple pigmentation of the stems. The photograph also shows the unique immature foliage variegation of the new variety.
2. The photograph at the bottom of the sheet is a side-by-side comparison of (from left to right) 'Goldenglossy', *Abelia×grandiflora* 'Conti' U.S. Plant Pat. No. 8,472, and *Abelia×grandiflora* 'Sunrise' U.S. Plant Pat. No. 9,698. This photograph, which was taken in mid-summer, shows the compact growth habit, attractive white flowers, and the unique light green mature foliage of the new variety.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Abelia based on my observations made of 2 year old plants grown in 3 gallon containers in wholesale commercial production practices, in greenhouses, and in established landscape plantings in Loxley, Ala.

Distinctive Characteristics:

| Characteristic | 'Goldenglossy' | 'Sherwoodii' | 'Conti' | 'Sunrise' |
|---|---|---|---|---|
| Height (Mature) | 3–4' | 3–4' | 1½'–2' | 3–4' |
| Width (Mature) | 4–5' | 4–5' | 4–5' | 4–5' |
| Growth Habit | Compact | Compact | Ground cover | Compact |
| Leaf Length | ¾–1¼" | ¾–1¼" | ¾–1" | ¾–1" |
| Leaf Width | ⅜–⅝" | ⅜–⅝" | ⅜–⅝" | 5/16–½" |

-continued

Distinctive Characteristics:

| Characteristic | 'Goldenglossy' | 'Sherwoodii' | 'Conti' | 'Sunrise' |
|---|---|---|---|---|
| Leaf Variegation (Immature) | Yellow Group 10B | None | Greyed–Yellow G.160C | Greyed–Yellow G. 160A |
| Leaf Variegation (Mature) | Yellow–Green G. 144A | None | Greyed–Yellow G. 160C | Greyed–Yellow G. 160A |

The three cultivars listed above are comparable to the new cultivar, however, there are many differences. *Abelia×grandiflora* 'Conti' U.S. Plant Pat. No. 8,472 has a ground cover growth habit and retains its cream-white variegation throughout the year. *Abelia×grandiflora* 'Sunrise' U.S. Plant Pat. No. 9,698 also maintains its yellow variegation throughout the year. The parent cultivar *Abelia×grandiflora* 'Sherwoodii' is not variegated. 'Goldenglossy' is unique in that as the leaf matures the variegation turns an attractive light green color. Under normal growing conditions in Loxley, Ala. this takes 6 to 8 weeks. 'Conti', 'Sherwoodii', and 'Goldenglossy' produce many flowers even as young plants, whereas the cultivar 'Sunrise' produces few flowers.

Classification:

*Botanical.*—*Abelia×grandiflora* 'Goldenglossy'.

*Parentage.*—Branch sport of *Abelia×grandiflora* 'Sherwoodii'.

*Commercial.*—Broadleaf evergreen to semi-evergreen.

*Form.*—Compact.

*Height.*—3–4'.

*Width.*—4–5'.

*Growth rate.*—Medium to fast under normal fertilization and moisture conditions. Mature height is 3–4' and width 4–5'. This is comparable to the parent cultivar. Rooted cuttings can be produced in 2–3 months when propagated in late spring in Loxley, Ala. Root development is vigorous and finely branched. From a rooted cutting, the new variety reaches a height of 3' and a spread of 3' in a period of four years. Under normal growing conditions in Loxley, Ala., the growth rate is normally about 8–10" per year while maintaining a dense habit due to the abundant branch development and short internode lengths.

*Foliage.*—Opposite, simple, ovate, evergreen to semi-evergreen, ¾ to 1¼" long and ⅜ to ⅝" wide. Apex is acute to broadly acute; the base is attenuate; the margins are crenate to slightly serrate above the widest portion of the leaf. The petioles are 1/16 to 3/16" long, 1/32" in diameter, and Red-Purple Group 60A. The upper surface of the leaf is glossy and glabrous. The underside is glabrous and matte. Leaf venation is pinnate. Mid-ribs are impressed on the upper surface and the primary lateral veins are obscure. Mid-ribs are prominent on the underside, 3 to 5 lateral veins are conspicuous and the secondary veins are reticulate. As the new foliage emerges it is pronounced with a reddish-orange coloration (Greyed-Orange Group 169A) which lasts 3–4 weeks.

The leaves are variegated and contain three primary colors: a yellow color (Yellow Group 10B) which generally extends inwardly from the margins of the leaves, a deep green color (Yellow-Green Group 147A) which usually is expressed in the central portion of the leaves covering more of less 75% of the total leaf surface area, and a combination of the two (Yellow-Green Group 144B) where one or more layers of cells of yellow overlay a layer of green cells. The color, Yellow Group 10B, covers approximately 20% of the total leaf surface area and the Yellow-Green Group 144B covers approximately 5%. This variegation pattern varies from leaf to leaf and is probably derived from two or more genetically distinct histogenic regions of the leaf forming meristem and is thought to represent a periclinal type of chimera. Differences in chlorophyll content in regions of the leaf result in different colorations. The variegation pattern is followed on the underside of the leaf with the three primary colors: a yellow color (Yellow Group 10C), a green color (Green Group 137D), and a combination of the two (Yellow-Green Group 145B). In a period of 6–8 weeks the immature yellow variegation, Yellow Group 10B, changes to Yellow-Green Group 151B and finally to Yellow-Green Group 144A. The combination color Yellow-Green Group 144B matures to Yellow-Green Group 147B. The central deep green color (Yellow-Green Group 147A) is persistent.

Light exposure affects foliage color. Plants grown in low light conditions (approximately 50% shade) produce the immature foliage colors Yellow-Green Group 144A–B, Yellow-Green Group 147B, and Yellow-Green Group 147A. These colors are similar to the mature foliage colors produced in full sun. The immature foliage coloration Greyed-Orange Group 169A is present but less pronounced than plants grown in full sun.

With the onset of cool weather in the fall, the leaf consists of the color Greyed-Orange Group 171A which changes to Greyed-Red Group 179A in the winter. The central deep green (Yellow-Green Group 147A) is persistent.

In 1999, the date of initial spring growth was March 2, in Loxley, Ala. It had been a mild winter and the plants were almost completely evergreen. The previous winter had been cold and approximately ⅓ of the foliage was shed in mid-January. After the initial spring flush, there was almost continuous growth until fall, ending October 15, also in Loxley, Ala. This growth pattern was identical to the parent cultivar. When grown in full sun, the internode length of 'Goldenglossy' is ¼" to ½". When grown in light shade, the internode length is ⅜" to ¾". This is identical to the parent cultivar. As would be expected, either plant grown in the shade results in a taller, less dense plant with larger leaves.

Stems: Young stems are pubescent with a pronounced reddish-purple pigmentation (Purple-Red Group 60A). In about a month this color changes to Greyed-Purple Group 183A. After one or more years, the stems are exfoliating and split to expose a light inner bark which is Greyed-Green Group 196B. The plant is densely branched throughout the entire shrub. The pith is solid and uniform.

Flowers: Perfect, single, fragrant, ½" to ¾" long, ⅜" to ½" in diameter, produced in loose terminal panicles on current season's growth. The corolla is gamopetalous, campanulate-funnel form, distally 4 to 5-lobed, and White Group 155D. The pistil is single, ½" to ¾" long and White Group 155C. The ovary is Yellow-Green Group 145D and inferior. There are 2 to 4 stamens 3/16" to ⅜" long. The filaments are White Group 155C. The anthers are 1/16" long, Yellow-White Group 158C, and the pollen is White Group 155B. Pedicels are ⅛" to ¼" long and Red-Purple Group 60A. There are 3 to 5 sepals, 1/16" to 3/16" long, 1/32"

to 1/16" wide, and Greyed-Red Group 180B. Sepals are not persistent.

There is a two to three week flowering period normally beginning in early June in Loxley, Ala. There is sporadic flowering in the summer and fall. The blooms last on the plant in the garden five to seven days. A mature plant may have several hundred flowers. Flowers have a sweet fragrance.

Fruit: None have been observed.

Culture: Grows well in a wide range of conditions and tolerates sun to shade. Prefers a moist, well-drained soil that is rich in organic matter but is adaptable; responds well to mulching and medium applications of fertilizer; prefers ph 5.0 to 6.5; best flowering in full sun but will grow and flower in shade; very little pruning is needed. Cold hardiness and drought resistance are comparable to the parent cultivar. Propagated with semi-hardwood cuttings in late spring through the summer.

Disease and insect resistance: Resistance to diseases and insects common to plants of Abelia has not been observed.

I claim:

1. A new and unique variety of *Abelia×grandiflora* plant named 'Goldenglossy' as herein shown and described.

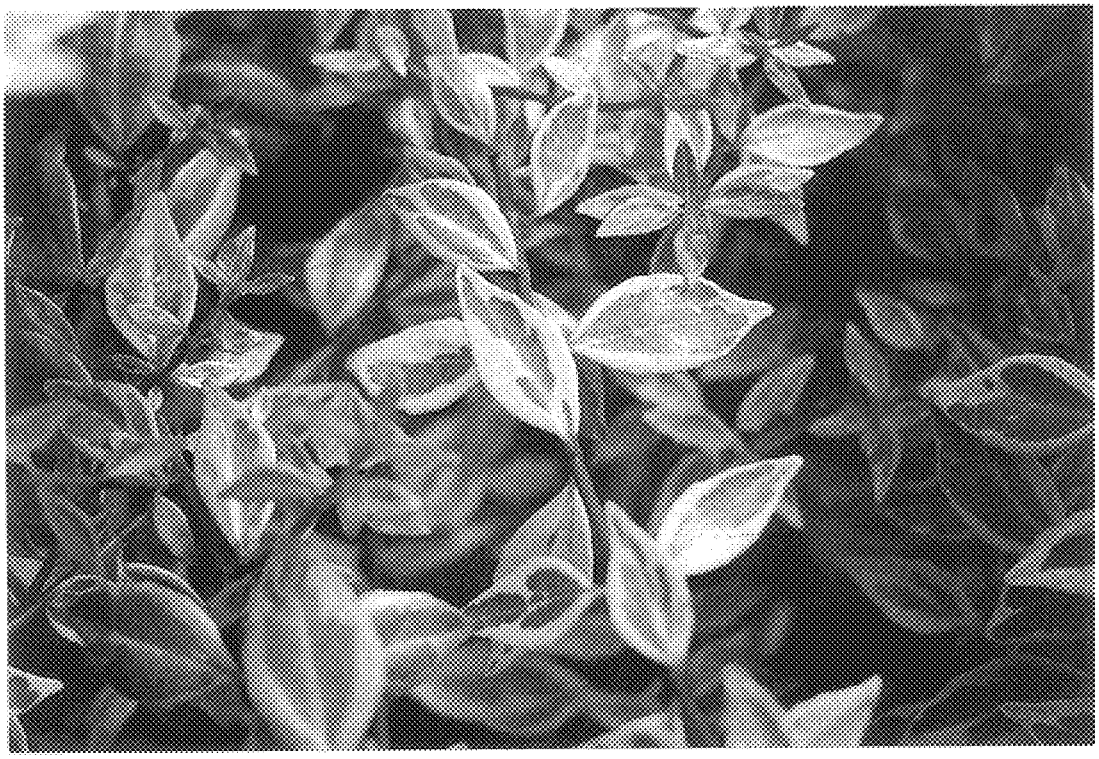
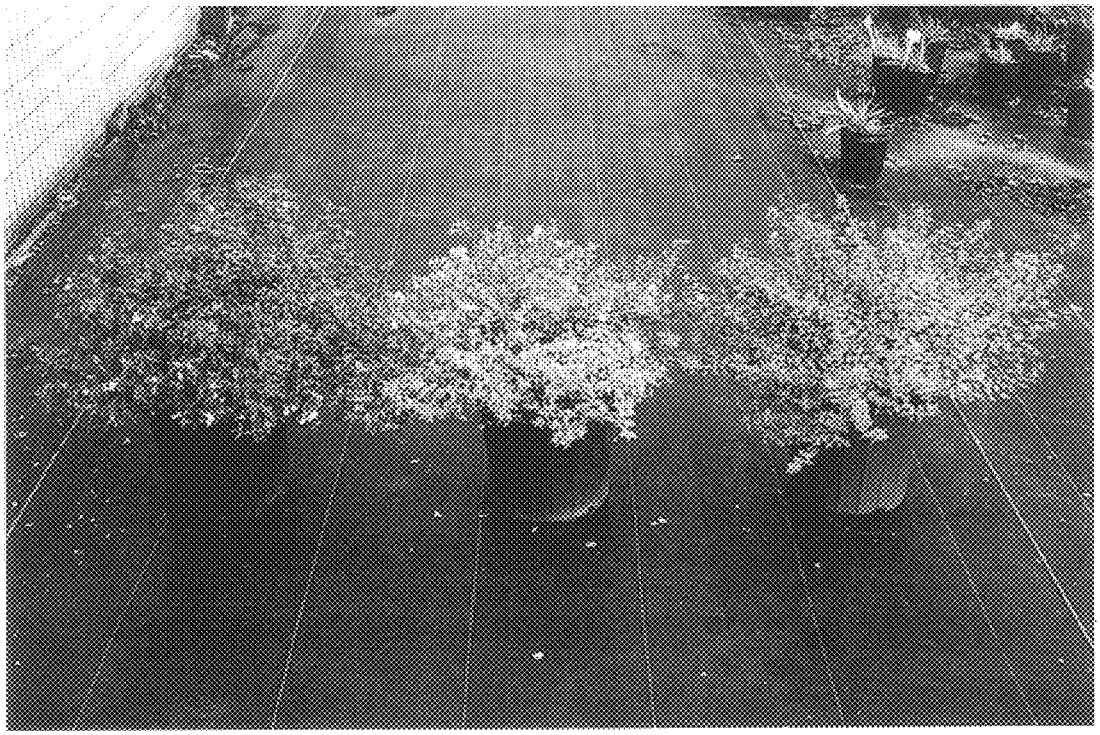

* * * * *